(12) United States Patent
Hebert

(10) Patent No.: US 6,734,210 B2
(45) Date of Patent: May 11, 2004

(54) THERAPEUTICALLY IMPROVED SALTS OF AZELAIC ACID

(76) Inventor: Rolland F. Hebert, 427 Bellevue Ave. E., #301, Seattle, WA (US) 98102

( * ) Notice: Subject to any disclaimer, the term of this patent is extended or adjusted under 35 U.S.C. 154(b) by 78 days.

(21) Appl. No.: 09/791,358

(22) Filed: Feb. 23, 2001

(65) Prior Publication Data

US 2001/0034321 A1 Oct. 25, 2001

Related U.S. Application Data

(60) Provisional application No. 60/184,750, filed on Feb. 24, 2000.

(51) Int. Cl.$^7$ ............................................. A61K 31/35
(52) U.S. Cl. .................... 514/460; 514/165; 514/859; 514/55; 530/427; 528/183
(58) Field of Search .................. 514/55, 859, 165; 428/401; 528/83; 530/427

(56) References Cited

U.S. PATENT DOCUMENTS

| | | |
|---|---|---|
| 4,292,326 A | 9/1981 | Nazzaro-Porro |
| 4,386,104 A | 5/1983 | Nazzaro-Porro |
| 4,713,394 A | 12/1987 | Thornfeldt |
| 4,818,768 A | 4/1989 | Nazzaro-Porro |
| 4,885,282 A | 12/1989 | Thornfeldt |
| 5,549,888 A | 8/1996 | Venkateswaran |
| 5,874,463 A * | 2/1999 | Ancira ....................... 514/460 |
| 6,451,773 B1 | 9/2002 | Oester |

OTHER PUBLICATIONS

Mortensen, P.B. "Dicarboxylic Acids and the Lipid metabolism" Danish Medical Bulletin, Vol 31, #2/Apr., 1984 121–145.

Schollreuyer, Karin Acelaic Acid as a Competitive Vahibitor of thioredeon reductase in human melanoma Cells. Cancer Letters, Vol 36, (1987) 297–305. Elsevier Scientific Ireland.

Galhup, I. Acelaic Acid: Mode of Action at Cellulose and Subcellular levels. Acta. Derm Vanereal (Stockh) 1989:Suppl 143: 75–82.

Passi, S. Azelaic Acid—Biochemistry and Metabolism. Acta Derm Veneral (Stockh) 1989 Suppl (143), 8–13.

Stamatidis, D. Inhibition of Sareductase activity in human skin by zinc and azelaic acid. British Journal of Dermatology (1988) vol 119, 627–632.

Fitton, A. Azelaic Acid. A review of its Pharmacological Properties and Therapeutic Efficacy in Acne and hyper psymantory–disorders. Drugs, 41 (5) 780–798 1991.

Maddin, S. A Comparison of topral azelaic acid 20% cream and topical metronidazole 0.75% cream in the treatment of patients with papulopustulbu rosacea. J. Am Acad Dermatol, 1999:40:961–5.

Zaffaroni, N. Cytotoxic Activity of Agelaic Acrdagainst known melanoma, primary centures and metablished cell lines. Anticancer Research, 10, 1599–1602 (1990).

Breathnad, A.S. Effect of Dickrbryzle Acids ($C_6$ and $C_9$) on Human Chorosidal Melanomarncellutine. Investigative Optalomolgy & Visual Science vol. 30, No. 3, Mar., 1986 pp 491–498.

* cited by examiner

*Primary Examiner*—Christopher Tate
*Assistant Examiner*—Roy Teller

(57) ABSTRACT

Stable salts of azelaic acid with polycations such as chitosan are described. The salts according to the invention are water-soluble, therapeutically more efficacious and are valuable for use as active constituents in pharmaceutical as well as cosmeceutical compositions.

5 Claims, No Drawings

THERAPEUTICALLY IMPROVED SALTS OF AZELAIC ACID

BACKGROUND-CROSS-REFERENCES TO RELATED APPLICATION

This application claims the benefit of Provisional Patent Application Serial Number: 60/184,750 filed on Feb. 24, 2000.

FIELD OF THE INVENTION

The present invention relates to new water-soluble salts of azelaic acid.

1. Technical Field

This patent relates to new salts of azelaic acid with polycations, the processes for obtaining them and to therapeutic uses of these new salts. More particularly, the invention relates to salts deriving from the reaction between azelaic acid and polycations such as chitosan, their production process, and pharmaceutical compositions that contain them as active principles.

2. Background of the Invention

Azelaic acid is a naturally occurring straight-chained, 9-carbon atom saturated dicarboxylic acid obtained by oxidation of oleic acid and by chemical, physical or biological oxidation of free and esterified fatty acids. It is found also in small amounts in the urine of normal individuals (Mortensen P. B. Dicarboxylic acids and the lipid metabolism. Danish Med Boll 1984; 31:121–145). In vitro, azelaic acid has been shown to be a competitive inhibitor of a number of oxidoreduction enzymes such as tyrosinase (Nazzaro-Porro M., Passi S., Morpugro G., Breatimach A. S. Identification of tyrosinase inhibitors in cultures of Pityrosporum, and their melanocytotoxic effect. In: Klaus S. N. (Ed). Pigment Cell, Vol1, Basel: Karger, 1979; 234–243.), thioredoxin reductase (Schallreuter K. U., Wood J. M. Azelaic acid as a competitive inhibitor of thioredoxin reductase in melanoma cells. Cancer Letters 1987;36:297–305.), DNA polymerase (Galhaup I. Azelaic acid: mode of action at cellular and subcellular levels. In: Breathnach A. S., Graupe K., Stingl G. (Eds.) Azelaic acid: A New Therapeutic Agent. Acta Derm Venereol Stockh 1989; 43 (Suppl): 75–82.) and also of mitochondrial oxidoreductases in the respiratory chain. (Passi S., Picardo M., Nazzaro-Porro M., Breathnach A. S. et al. Antimitrochondrial effect of medium chain length (C8–C13) dicarboxylic acids. Biochem Pharmacol 1984; 33:103–108.) In addition, azelaic acid is a potent inhibitor of 5-alpha-reductase (Stamatidas D., Bulteau-Portois M. C., Moszowicz I. Inhibition of 5-alpha reductase activity in human skin by zinc and azelaic acid. Br. J Dermatol 1988;118: 627–632.) Azelaic acid is a scavenger of toxic oxygen species and also inhibits oxyradical activity in cell cultures. (Passi S., Picardo M., De Luca C. et al. Scavenging activity of azelaic acid on hydroxyl radicals in vitro. Free Rad Res Comm 1991; 11:329–339. Passi S., Picardo M., Zompetta C., et al. Oxyradicals scavenging activity of azelaic acid in biological systems. Free Rad Res Comm 1991;15: 17–28.)

Azelaic acid has been used clinically for many years in the treatment of acne vulgaris as well as in hyperpigmentary skin disorders. (Fitton A. and Goa, K. L. Azelaic acid: A Review of its Pharmacological Properties and Therapeutic Efficacy in Acne and Hyperpigmentary Skin Disorders. Drugs 41 (5): 180–798, 1991) It has recently been studied for the treatment of papulopustular rosacea (Maddin, S. A comparison of topical azelaic acid 20% cream and topical metronidazole 0.75% cream in the treatment of patients with papulopustular rosacea. J Am Acad Dermatol 1999;40: 961–965)

While azelaic acid has been used primarily in the treatment of dermatological conditions, because of some of its mechanisms of action, it could have further clinical utility in conditions unrelated to the skin. Azelaic acid has been shown to have antiproliferative and cytotoxic action on the following tumor cell lines: human cutaneous malignant melanoma (Zaffaroni N., Villa R., Silvestro L et al. Cytotoxic activity of azelaic acid against human primary melanoma cultures and established cell lines. Anti Can Res 1990;10:1599–1602.), human choroidal melanoma (Breatimach A. S., Robins E. J., Patzhold H. C. et al. Effect of dicarboxylic acids (C6,C9) on human choroidal melanoma in cell culture. Invest Ophthal Vis Sci 1989;30: 491–498), human squamous cell carcinoma (Paetzold H. C., Breathnach A. S., Robins E. J., et al. Effect of dicarboxylic acids (C6C9) on a human squamous carcinoma line in culture. Histo Histopathol 1989;4: 167–171.) and fibroblastic lines (Geier G., Haushild T., Bauer R et al. Der Einfluss von Azelainsaure auf das Wachstum von Melanomazelikulturen im Vergleich zu Fibroblastemkulturen. Hautartz 1986;37: 146–148.). Azelaic acid would also be expected to have utility in the prevention and treatment of skin cancer as well as solar keratosis. Because of its mechanism of action as a potent inhibitor of 5-alpha reductase, azelaic acid may be applicable to the treatment and prevention of benign enlargement as well as cancer of the prostate and other conditions in which 5-alpha reductase is elevated.

While azelaic acid is somewhat soluble in water, cosmetic oils and alcohols, each of these solvents has serious limitations. Thus, water only marginally dissolves azelaic acid so that a water and azelaic acid solution would contain a maximum of about 0.24% by weight (w/w) azelaic acid, not likely enough to be effective. Azelaic acid has little or no solubility in cosmetic oils. Alcohols are good solvents but are unsatisfactory because large amounts of alcohol e.g., isopropyl alcohol, in a topical composition have the undesirable side effect of drying the skin. Indeed, some alcohols e.g., ethyl alcohol, render azelaic acid unstable at normal temperatures resulting in a totally ineffective composition. For the dermatological use of azelaic acid, the problem of solubility in suitable solvents remains.

U.S. Pat. No. 4,292,326 (Nazzaro-Porro, Sep. 29, 1981), U.S. Pat. No. 4,386,104 (Nazzaro-Porro, May 31, 1983), and U.S. Pat. No. 4,818,768 (Nazzaro-Porro, Apr. 4, 1989) describe azelaic acid as well as other dicarboxylic acids in the treatment of acne and melanocyclic hyperpigmentary dermatoses. The azelaic acid is dispersed in a cream base. These patents do not disclose the use of new azelaic acid salts of the present invention made with chitosan.

U.S. Pat. No. 4,713,394 (1Thomfeldt, Dec. 15, 1987) and U.S. Pat. No. 4,885,282 (Thornfeldt, Dec. 5, 1989) describe azelaic acid as well as other dicarboxylic acids used in the treatment of non-acne inflammatory dermatoses and infectious cutaneous diseases such as rosacea, perioral dermatitis, eczema, seborrheic dermatitis, psoriasis, tinea cruris, flat warts, and alopecia areata. One of Thomfeldt's formulations comprises azelaic acid disposed in a large proportion of ethanol. While ethyl alcohol dissolves azelaic acid, it also renders the azelaic acid unstable at normal temperatures meaning that it will not provide a marketable product. Thornfeldt's second formulation comprises a complete dispersion of azelaic acid. These patents do not disclose the use of new azelaic acid salts made with chitosan.

Venkateswaran U.S. Pat. No. 5,549,888 teaches a solution of active ingredients which includes azelaic acid and is partially solubilized by a glycol. It uses glycol in combination with ethyl alcohol to solubilize the azelaic acid. As stated previously, the presence of ethyl alcohol with azelaic acid can destabilize the azelaic acid. Moreover, because the composition contains ethyl alcohol, formulation of a non-drying, aesthetically pleasing formulation would be difficult. Venkateswaran also teaches that the formulation has a pH between 2.5 and 4.0. This low pH range can have an irritating effect on the skin. Again, this patent also does not teach the use of new azelaic acid salts made with chitosan. Indeed, a search of the patent as well as the scientific literature does not reveal any prior use of the salts of azelaic acid that are the object of this present invention.

The art has yet to find a formulation for completely solubilizing azelaic acid at normal temperatures without sacrificing the stability of the solubilized azelaic acid. Solubilized azelaic acid must remain stable at normal temperatures in order to provide a marketable product.

Without a stable, completely solubilized formula of azelaic acid, the benefits of azelaic acid are unavailable to many users who experience the burning, stinging and redness of the skin associated with exposure to high levels of undissolved dispersed azelaic acid having an inherent low pH. The present invention provides a completely water soluble and stable salt of azelaic acid.

In addition, the new water-soluble azelaic acid salts may be more bioavailable when administered by routes other than the topical one. These new salts of the present invention would have significant utility over salts of azelaic acid currently described in the patent and scientific literature. These and still further objects as shall hereinafter appear are fulfilled by the present invention in a remarkably unexpected fashion.

Accordingly, there is need in the art for new, water-soluble salts of azelaic acid as well as methods related to the use of such salts. There is also a need in the art for synthetic routes to make such new salts. The author of this present invention fulfills these needs, provides further related advantages, and has surprisingly and unexpectedly solved the problem of solubility of azelaic acid with the synthesis of new salts of azelaic acid.

SUMMARY OF THE INVENTION

Briefly stated, the present invention discloses new, water soluble salts of azelaic acid, methods for the use thereof and synthetic methods for their preparation. These new salts of azelaic acid of this present invention have utility in increasing blood and other tissue or fluid levels of azelaic acid, as well as treating or preventing a wide variety of conditions related to the aforementioned mechanisms of action of azelaic acid. Thus in one embodiment, a new azelaic acid salt is administered to a warm-blooded animal in need thereof In yet a further embodiment, a new azelaic acid salt is administered to a warm blooded animal to prevent and or treat the following conditions: aging of the skin, cancer, HIV, alopecia, solar keratosis, benign prostatic hypertrophy, prostate cancer, acne, malignant melanoma, hair loss, bladder cancer, rosacea, conditions in which tyrosinase activity needs to be modulated, melasma, conditions in which 5-alpha reductase activity needs to be modulated, conditions related to excessive expression of reactive oxygen species, lentigo maligna, hyperpigmentation associated with burns and other physical trauma, viral infections, and herpes labialis. Other aspects of the present invention will become evident upon reference to the following detailed description.

DETAILED DESCRIPTION OF THE INVENTION

As mentioned above, this invention is generally directed to new water-soluble salts of azelaic acid. Such new azelaic acid salts, when administered to a warm blooded animal in need thereof, have utility in the prevention or treatment of conditions enumerated above in warm blooded animals, including humans.

The term "treat" or "treatment" means that the symptoms associated with one or more conditions mentioned above are alleviated or reduced in severity or frequency and the term "prevent" means that subsequent occurrences of such symptoms are avoided or that the frequency between such occurrences is prolonged.

It has now surprisingly been found that salts of azelaic acid with chitosan have good characteristics that are such as to render them particularly suitable both for use in pharmaceutical formulations and for preparative applications.

Owing to their simple conception and low costs, the procedures described in this invention easily lend themselves to working out methods of preparation on an industrial scale.

The examples given herein below illustrate the preparation of two salts of azelaic acid with chitosan. Only a few of the many possible embodiments that may be anticipated are shown by these examples which are intended to define, in a non-limiting sense, the scope encompassed by the invention. The examples further illustrate the antibacterial action of this compound and the complete absence of side effects when a 20% cream is applied topically to the forearm of healthy volunteers.

These examples are given to illustrate the present invention, but not by way of limitation. Accordingly, the scope of this invention should be determined not by the embodiments illustrated, but rather by the appended claims and their legal equivalents.

EXAMPLE 1

Azelaic acid (0.11 g) was stirred in water (10 ml) and chitosan (0.10 g, degree of deacetylation 80.1%) was added with stirring. The solution was stirred until dissolved. The solution was filtered and dried.

EXAMPLE 2

Azelaic acid (0.11 g) was stirred in water (15 ml) and chitosan (0.20 g, degree of deacetylation 80.1%) was added with stirring. The solution was stirred until dissolved. The solution was filtered and dried.

Azelaic acid and chitosan are available commercially from Sigma Chemical Company, St. Louis, Mo.

EXAMPLE 3

Minimum inhibitory concentration of the new azelaic acid salt Propionibacterium acnes was tested. Serial 2-fold dilutions of 282 grams/l of azelaic acid salt of example 2 were made in 2 ml of the appropriate nutrient broth for this organism. Each tube was then seeded with 0.02 ml of the inoculum (5 day anaerobic culture of propionibacteria in Reinforced Clostridial Medium (Oxoid)). After incubation for an appropriate period (7 days), growth was assessed by eye, and 0.1 ml of the broth showing no visible growth was spread over the surface of a suitable recovery medium to ascertain if viable cells were present. The minimum inhibitory concentration (MIC) was the greatest dilution at which no viable organisms were recovered. MIC of the azelaic acid salt of example 2 in this experiment is 101.5 grams/l (0.18 mol/l of azelaic acid).

EXAMPLE 4

A 20% cream made of this new salt of azelaic acid was applied to the forearm of 10 healthy individuals twice daily for a two-week period in an outpatient clinic. No patients complained of burning, irritation, scaling or redness after the cream. Patients returned to the clinic after having used the cream for two weeks for a visual inspection of the forearm area. The examining physician noted no redness, irritation or scaling in the area where the cream had been applied.

I claim:

1. A composition useful for the treatment of acne and rosacea comprising an effective amount of a mixture of azelaic acid and chitosan whereby the mixture is prepared by mixing azelaic acid and chitosan in water to form a solution and drying the solution.

2. The composition of claim 1 wherein the amount of chitosan is between 0.01% to 100% of the weight of azelaic acid.

3. The composition of claim 1 wherein the amount of chitosan is between 10% to 100% of the weight of azelaic acid.

4. The composition of claim 1 wherein the amount of chitosan is between 30% to 60% of the weight of azelaic acid.

5. The composition of claim 1 wherein the amount of chitosan is between 40% to 50% of the weight of azelaic acid.

* * * * *